United States Patent [19]

Watanabe et al.

[11] Patent Number: 5,026,842
[45] Date of Patent: Jun. 25, 1991

[54] PROCESS FOR PREPARING CEPHALOSPORIN COMPOUNDS

[75] Inventors: Kazuhiro Watanabe; Husayoshi Kakizaki; Isao Arai, all of Kawasaki; Kimihiro Murakami, Gotenba; Kazuo Kato, Mishima, all of Japan

[73] Assignees: Ajinomoto Co., Inc.; Mochida Pharmaceutical Co., Ltd., both of Tokyo, Japan

[21] Appl. No.: 373,268

[22] Filed: Jun. 28, 1989

[30] Foreign Application Priority Data

Jun. 28, 1988 [JP] Japan ................... 63-158022

[51] Int. Cl.$^5$ ............................. C07D 501/06
[52] U.S. Cl. .................... 540/222; 540/221; 540/227; 540/225
[58] Field of Search ............... 540/222, 226, 227, 221

[56] References Cited

U.S. PATENT DOCUMENTS 4,614,819  9/1986  Nagai et al. .................. 540/228
4,888,332  12/1989  Ohnishi et al. ................ 514/206

FOREIGN PATENT DOCUMENTS 60-142987  6/1985  Japan .

Primary Examiner—Nicholas S. Rizzo
Attorney, Agent, or Firm—Oblon, Spivak, McClelland, Maier & Neustadt

[57] ABSTRACT

Reaction of a 7-aminocephalosporanic acid with a carboxylic acid in the presence of a dehydration condensing agent and an acid or acid complex provides the corresponding amide in high yield and high purity.

2 Claims, No Drawings

PROCESS FOR PREPARING CEPHALOSPORIN COMPOUNDS

BACKGROUND OF THE INVENTION

1. Field of the Invention

The present invention relates to a process for preparing amide compounds, which are utilizable for production of 7-substituted-amino-3-substituted-methylcephem-carboxylic acids, which in turn are useful as drugs such as antibiotics or intermediates thereof.

2. Discussion of the Background

It is known that amide compounds can be prepared by reacting 7-aminocephalosporanic acids with carboxylic acids in the presence of a dehydration condensing agent, for example, dicyclohexylcarbodiimide, first Publication No. 142987/1985 Japan. However, the poor yields by this process present a problem when the process is used on an industrial scale.

Thus, there remains a need for a process for preparing amides in high yield which can be applied on an industrial scale in a simple manner. There also remains a need for a process for preparing amides of 7-aminocephalosporanic acids in high yield. In particular, there remains a need for a process for preparing 7-substituted-amino-3-substituted-methylcephem-carboxylic acids in high yield which can be applied on an industrial scale.

SUMMARY OF THE INVENTION

Accordingly, it is an object of the present invention to provide an industrial process which can produce highly pure amide compounds in a simple manner in a high yield.

It is another object of the present invention to provide a process for preparing amides of 7-aminocephalosporanic acids in high yield which can be applied on an industrial scale.

It is another object of the present invention to provide a process for preparing 7-substituted-amino-3-substituted-methylcephem-carboxylic acids in high yield which can be applied on an industrial scale.

As a result of extensive investigations to solve the foregoing problem, the present inventors have found that these and other objects, which will become apparent during the course of the following detailed description, can be achieved by reacting 7-aminocephalosporanic acid derivatives with carboxylic acids in the presence of dehydration condensing agents and acids or acid complexes.

DETAILED DESCRIPTION OF THE PREFERRED EMBODIMENTS

As the dehydration condensing agent, any compound is suitable so long as it is conventionally used for amidation. Thus, for example, carbodiimides represented by the formula: $R^1-N=C=N-R^2$ may be used; wherein $R^1$ and $R^2$, which may be the same or different, each represents a substituted or unsubstituted alkyl group having 1 to 5 carbon atoms, a substituted or unsubstituted aryl group having 6 to 10 carbon atoms, a substituted or unsubstituted cycloalkyl group having 6 to 10 carbon atoms, or a substituted or unsubstituted aralkyl group having 7 to 20 carbon atoms.

The acid or the acid complex is selected from a sulfonic acid represented by the formula: $R^3SO_3H$, a hydrohalogen acid represented by HX, a Lewis acid or a Lewis acid complex; wherein $R^3$ represents a hydroxy group, a substituted or unsubstituted alkyl group having 1 to 5 carbon atoms, a substituted or unsubstituted aryl group having 6 to 10 carbon atoms, a substituted or unsubstituted cycloalkyl group having 6 to 10 carbon atoms, or a substituted or unsubstituted aralkyl group having 7 to 20 carbon atoms; and X represents a halogen atom.

Examples of the Lewis acid include halogen compounds of aluminum, tin, zinc, boron or titanium. Examples of the Lewis acid complex include dialkyl ether complexes with diethyl ether, di-n-propyl ether, di-n-butyl ether, etc.; fatty acid complexes with acetic acid, propionic acid, etc.; nitrile complexes with acetonitrile, propionitrile, etc.; carboxylic acid ester complexes with ethyl acetate, etc.; phenol complexes with phenols, etc.

When a solvent is used, there may be used, for example, a halogen-containing organic solvent such as dichloromethane, chloroform, carbon tetrachloride, 1,2-dichloroethane, 1,1,1-trichloroethane, etc.; an alcoholic organic solvent such as methanol, ethanol, isopropyl alcohol, etc.; a ketone organic solvent such as acetone, methyl ethyl ketone, acetophenone, etc.; an ether organic solvent such as tetrahydrofuran, diethyl ether, dioxane, etc. These solvents may also be used in admixture of two or more.

Utilizing the present invention, 7-substituted-amino-3-substituted-methylcephem-carboxylic acids can also be prepared.

That is, a 7-aminocephalosporanic acid derivative represented by the general formula (I):

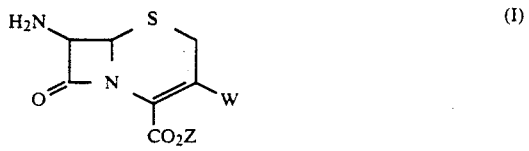

wherein W represents a hydrogen atom, ethenyl, 2-carboxyethenyl, chlorine, methoxy or a functional group represented by $-CH_2Y$, wherein Y represents a hydrogen atom or a nucleophilic compound residue, and Z represents a hydrogen atom, a metal atom, or a substituted or unsubstituted alkyl group having 1 to 5 carbon atoms, a substituted or unsubstituted aryl group having 6 to 10 carbon atoms, a substituted or unsubstituted cycloalkyl group having 6 to 10 carbon atoms, or a substituted or unsubstituted aralkyl group having 7 to 20 carbon atoms, is reacted with a compound represented by general formula (IV):

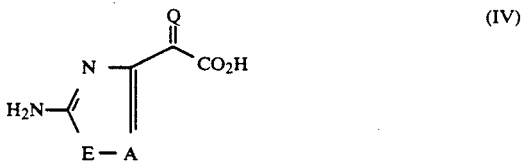

in which A represents

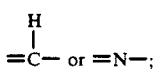

E represents $-S-$ or $-O-$; Q represents $=O$ or a functional group represented by $=N\sim R^4$ (wherein $R^4$ represents a hydroxy group or an alkoxy group which may optionally be substituted; and $\sim$ in $=N\sim R^4$ represents syn- or anti-form); in an organic solvent in the presence of a dehydration condensing agent represented by general formula (II):

wherein $R^1$ and $R^2$, which may be the same or different, each represents a substituted or unsubstituted alkyl group having 1 to 5 carbon atoms, a substituted or unsubstituted aryl group having 6 to 10 carbon atoms, a substituted or unsubstituted cycloalkyl group having 6 to 10 carbon atoms, or a substituted or unsubstituted aralkyl group having 7 to 20 carbon atoms, and an acid, for example, a sulfonic acid represented by general formula (III):

wherein $R^3$ represents a hydroxy group, a substituted or unsubstituted alkyl group having 1 to 5 carbon atoms, a substituted or unsubstituted aryl group having 6 to 10 carbon atoms, a substituted or unsubstituted cycloalkyl group having 6 to 10 carbon atoms, or a substituted or unsubstituted aralkyl group having 7 to 20 carbon atoms; or a hydrohalogen acid represented by HX, wherein X is a halogen atom, or a Lewis acid or a Lewis acid complex; to give a compound represented by general formula (V):

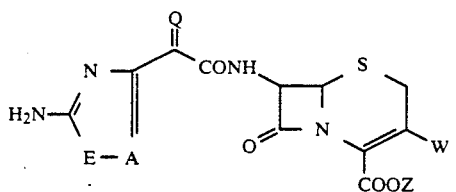

wherein A, E, Q, W, and Z have the same meanings described above, in a high yield and high purity by industrially simple procedures.

Many methods are known for reacting the amino group at the 7-position of 7-aminocephalosporanic acids with a carboxylic acid, salt, or acid halide thereof to derivatize the 7-position. However, the amino group-containing compounds shown in formula IV, in only a very few cases, give the product in a high yield by conventional condensation.

Examples of the nucleophilic compound residue represented by Y in the symbol W in formulas I and V include hydroxy, mercapto, carbamoyl, cyano, azido, amino, carbamoyloxy, carbamoylthio or thiocarbamoyloxy which may optionally be substituted with an alkyl (methyl, ethyl, propyl, etc.), an acyloxy (acetyloxy, propionyloxy, butyryloxy, benzoyloxy, p-chlorobenzoyloxy, p-methylbenzoyloxy, etc.); a quaternary ammonium group; or hydroxyphenyl, sulfamoyloxy, an alkylsulfonyloxy, (cis-1,2-epoxypropyl)phosphono, etc.

Y may also represent a hetero ring bound via S. In the present invention, the hetero ring refers to a 5- to 6-membered ring or a 7- to 14-membered fused ring containing 1 to 5 hetero atoms selected from O, S, and N.

Examples of the hetero ring which may be used include pyridyl, N-oxidopyridyl, pyrimidyl, pyridazinyl, N-oxidopyridazinyl, pyrazolyl, diazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, S-triazolo(1,5-a)pyrimidinyl, tetrazolo[1,5-b]pyridazinyl, pyrazolo(1,5-a)pyrimidinyl, isoindolyl, 1,2,4-triazinyl, 1,3,5-triazinyl, etc. These hetero rings may also be substituted with, for example, a lower alkyl group such as methyl, ethyl, propyl, etc., and it may also be formed with a cycloalkane fused to a hetero ring; a lower alkoxy group such as methoxy, ethoxy, etc.; a halogen such as chlorine, bromine, etc.; a halogeno-substituted alkyl such as trifluoromethyl, trichloromethyl, etc.; hydroxy group, mercapto group, amino group, carboxyl group, an ester group, carbamoyl group, carboxylmethyl group, carbamoylmethyl group, hydroxylmethyl group, etc.

Examples of the quaternary ammonium group which may be used include pyridinium, 3-methylpyridinium, 4-methylpyridinium, 3-chloropyridinium, 3-bromopyridinium, 3-iodopyridinium, 4-carbamoylpyridinium, 4-(N-carbomethoxycarbamoyl)pyridinium, 4-(N-cyanocarbamoyl)pyridinium, 4-(hydroxymethyl)pyridinium, 4-(carboxylmethyl)pyridinium, 4-(trifluoromethyl)pyridinium, quinolinium, picolinium, lutidinium, etc.

The $CO_2Z$ group in formulas I and V represents a carboxylic acid; a salt with an alkali metal or an alkaline earth metal, such as sodium, potassium, calcium, etc.; or an ester with an alkyl, aryl, or aralkyl group, such as methyl, ethyl, propyl, vinyl, phenyl, benzyl, diphenylmethyl, triphenylmethyl, etc. These esters may be substituted with have any substituent, so long as the substituent does not inhibit the reaction. In formula II, the alkyl, aryl, or aralkyl groups may be substituted with any substituent as long as the substituent does not inhibit the reaction in the present invention.

In formula III, $R^3$ represents a hydroxy, an alkyl, aryl, or aralkyl group, exemplified by methyl, ethyl, propyl, vinyl, camphanyl, phenyl, p-methylphenyl, etc. These groups may be substituted with any substituent as long as it does not inhibit the reaction.

Examples of the Lewis acid which can be used are halides of aluminum, tin, zinc, boron or titanium. As the complex of Lewis acid, mention may be made of a dialkyl ether complex with diethyl ether, di-n-propyl ether, di-n-butyl ether, etc.; a fatty acid complex with acetic acid, propionic acid, etc.; nitrile complexes with acetonitrile, propionitrile, etc.; carboxylic acid ester complexes with ethyl acetate, etc.; phenol complexes with phenols, etc. The alkoxy group in $R^4$ of formula IV may be substituted with any substituent, so long as the substituent does not inhibit the reaction.

The process of the present invention can be performed by reacting the compound of formula I with the carboxylic acid of formula IV in organic solvents in the presence of the dehydration condensing agent represented by formula II and the acid.

The solvent used for the reaction may be any organic solvent inasmuch as it does not adversely affect the reaction. Preferred examples are a halogen-containing organic solvent such as dichloromethane, chloroform, carbon tetrachloride, 1,2-dichloroethane, 1,1,1-trichloroethane, etc.; an alcoholic organic solvent such as methanol, ethanol, isopropyl alcohol, etc.; a ketone organic solvent such as acetone, methyl ethyl ketone, acetophenone, etc.; an ether organic solvent such as tetrahydrofuran, diethyl ether, dioxane, etc.; an ester organic solvent such as ethyl acetate, etc. These solvents may also be used in admixture of two or more.

The amount of the acid of formula III may be at least 0.1 equimolar, based on the number of moles of the compound of formula I. In general, the reaction rate greatly varies depending upon the solvent and carboxylic acid of formula IV. Therefore, it is desired that the amounts of the dehydration condensing agent shown by formula II and the acid of formula III be appropriately increased or reduced depending upon respective cases.

The reaction temperature is not particularly critical but is generally in a range of −20° to 10° C. and the reaction time is generally several minutes to several hours.

However, the reaction conditions described above are not limited thereto and may be appropriately chosen depending upon the reactants and solvent to achieve the object.

Other features of the invention will become apparent in the course of the following descriptions of exemplary embodiments which are given for illustration of the invention and are not intended to be limiting thereof.

EXAMPLES

EXAMPLE 1

Production of diphenylmethyl (6R,7R)-7-[2-(2-amino-4-thiazolyl)-2-[Z-[diphenylmethyloxycarbonyl(3,4-dihydroxyphenyl)methyl]oxyimino]acetamido]-3-[[2-diphenylmethyloxycarbonyl-5-methyl-s-triazolo(1,5-a)pyrimidin-7-yl]thiomethyl]-8-oxo-5-thia-1-azabicyclo[4.2.0]oct-2-ene-2-carboxylate:

In 25 ml of 1,2-dichloroethane, 3.78 g of diphenylmethyl (6R,7R)-7-amino-3-[[2-diphenylmethyloxycarbonyl-5-methyl-s-triazolo(1,5-a)pyrimidin-7-yl]thiomethyl]-8-oxo-5-thia-1-azabicyclo[4.2.0]oct-2-ene-2-carboxylate was dissolved. In 13 ml of methanol, 2.85 g of 2-(2-amino4-thiazolyl)-2-[Z-[diphenylmethyloxycarbonyl(3,4-dihydroxyphenyl)methyl]oxyiminoacetic acid was dissolved, and this solution was added to the 1,2-dichloroethane solution. To the resulting mixture was added 0.3 ml of methanesulfonic acid followed by stirring. The mixture was then cooled to 5° C. In 2 ml of 1,2-dichloroethane, 1.5 g of dicyclohexylcarbodiimide was dissolved, and the solution was dropwise added to the reaction solution. Forty minutes after the addition, the insoluble matter was removed by filtration. After the filtrate was concentrated, ethyl acetate was added to the residue and the insoluble matter was removed by filtration. After washing with saturated sodium chloride aqueous solution and drying over anhydrous sodium sulfate, the filtrate was concentrated, and the residue was purified by silica gel column chromatography to give 6.4 g of the title compound.

IR spectrum (KBr cm$^{-1}$): 1780, 1742, 1737, 1507, 1249, 1205, 1182

NMR spectrum (CDCl$_3$ ppm): 7.5–7.2 (35H, m), 7.0 (1H, s), 6.82 (1H, s), 6.76 (1H, s), 5.9 (1H, s), 5.8 (1H, dd), 4.9 (1H, d), 4.2 (2H, bs), 3.7 (2H, ABq), 2.6 (3H, s)

EXAMPLE 2

Production of diphenylmethyl (6R,7R)-7-[2-(2-amino-4-thiazolyl)-2-[Z-[diphenylmethyloxycarbonyl(3,4-dimethylmethylenedioxyphenyl)methyl]oxyimino]acetamido]-3-[[2-diphenylmethyloxycarbonyl-5-methyl-s-triazolo(1,5-a)pyrimidin-7-yl]thiomethyl]-8-oxo-5-thia-1-azabicyclo [4.2.0]-oct-2-ene-2-carboxylate:

In 30 ml of 1,2-dichloroethane, 3.78 g diphenylmethyl (6R,7R)-7-amino-3-[[2-diphenylmethyloxycarbonyl-5-methyl-s-triazolo(1,5-a)pyrimidin-7-yl]thiomethyl]-8-oxo-5-thia-1-azabicyclo[4.2.0]oct-2-ene-2-carboxylate was dissolved, and 2.90 g of 2-(2-amino-4-thiazolyl)-2-[Z-[diphenylmethyloxycarbonyl(3,4-dimethylmethylenedioxyphenyl)methyl]oxyiminoacetic acid was added to the solution, and further, 0.3 ml of methanesulfonic acid was added to the mixture. While stirring, the mixture was cooled to 5° C. In 2 ml of 1,2-dichloroethane, 1.5 g of dicyclohexylcarbodiimide was dissolved, and this solution was dropwise added to the reaction solution. Twenty minutes after the addition, the insoluble matter was removed by filtration. After the filtrate was concentrated, ethyl acetate was added to the residue, and the insoluble matter was removed by filtration. After washing with saturated sodium chloride aqueous solution and drying over anhydrous sodium sulfate, the filtrate was concentrated, and the residue was purified by silica gel column chromatography to give 6.3 g of the title compound.

NMR spectrum (CDCl$_3$ ppm): 7.5–7.1 (35H, m), 7.0 (1H, s), 6.9 (1H, s), 6.8 (1H, s), 5.9 (1H, s), 5.8 (1H, dd), 5.2 (1H, d), 4.4 (2H, bs), 3.5 (2H, ABq), 2.5 (3H, s), 1.6 (6H, s)

EXAMPLE 3

Production of diphenylmethyl (6R,7R)-7-[2-(2-amino-4-thiazolyl)-2-[Z-methoxyimino]acetamido]-3-acetoxymethyl-8-oxo-5-thia-1-azabicyclo[4.2.0]oct-2-ene-2-carboxylate:

In 25 ml of 1,2-dichloroethane, 1.83 g of diphenylmethyl (6R,7R)-7-amino-3-acetoxymethyl-8-oxo-5-azabicyclo[4.2.0]oct-2-ene-2-carboxylate was dissolved. To 25 ml of tetrahydrofuran was added 1.0 g of 2-(2-amino-4-thiazolyl)-2-[Z-methoxyimino]acetic acid, and the mixture was added to the 1,2-dichloroethane solution. To the resulting mixture was added 0.3 ml of methanesulfonic acid to dissolve. Furthermore, a solution of 1.5 g of dicyclohexylcarbodiimide in 2 ml of 1,2-dichloroethane was added to the solution. The mixture was then cooled to −5° C. and stirred for an hour. After the insoluble matter was removed by filtration and the filtrate was concentrated, ethyl acetate was added to the residue followed by filtration. After washing with saturated sodium chloride aqueous solution and drying over anhydrous sodium sulfate, the filtrate was concentrated. The residue was purified by silica gel column chromatography to give 2.91 g of the title compound.

NMR spectrum (CDCl$_3$ ppm): 7.5–7.1 (11H, m), 6.8 (1H, s), 5.8 (1H, dd), 5.1 (1H, d), 4.6 (2H, bs), 4.1 (3H, s), 3.7 (2H, ABq), 2.1 (3H, s)

EXAMPLES 4–7 AND COMPARATIVE EXAMPLE 1

The procedures of Example 1 were repeated, with the exception of using: p-toluenesulfonic acid, HCl, BF$_3$OEt$_2$, or H$_2$SO$_4$ as the acid. The results are shown in Table 1. For purpose of comparison, the results obtained with a case where no acid was added (Comparative Example 1) are also shown in Table 1.

TABLE 1

| Example | Compound (IV) | Compound (I) | Acid Added | Yield (%) |
|---|---|---|---|---|
| 4 | [structure: 2,2-dimethyl-benzodioxole-CH(CO₂CHPh₂)-O-N=C(aminothiazole)-CO₂H] | [structure: cephem with S-CH₂-C(=C(CO₂CHPh₂)-triazolyl-CH₃)] | 4-CH₃-C₆H₄-SO₃H | 97 |
| 5 | [structure: 3,4-dihydroxyphenyl-CH(CO₂CHPh₂)-O-N=C(aminothiazole)-CO₂H] | " | HCl | 98 |
| 6 | " | " | BF₃OEt₂ | 90 |
| 7 | " | " | H₂SO₄ | 77 |
| Comparative Example | " | " | — | 70 |

Solvent: 1,2-dichloroethane
Condensing Agent: dicyclohexylcarbodiimide

As is clear from the foregoing Examples, according to the present invention, the desired amide compounds can be produced from 7-aminocephalosporanic acid or derivatives thereof in a high yield and high purity by industrially simple procedures, and the present invention is extremely useful from an industrial standpoint.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process for preparing an amide compound, which comprises reacting a 7-aminocephalosporanic acid with a carboxylic acid in the presence of a dehydration condensing agent and at least a 0.1 equal molar amount of an acid or an acid complex, wherein said 7-aminocephalosporanic acid is represented by the formula

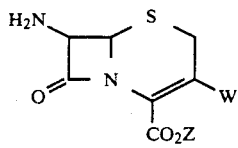

said carboxylic acid is represented by the formula:

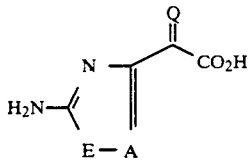

and said amide compound is a 7-substituted amino-3-substituted methylcephem-carboxylic acid represented by the formula:

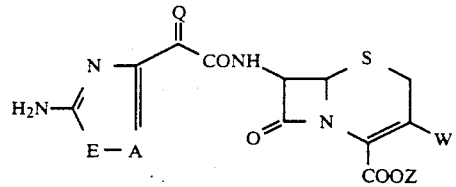

wherein W represents a hydrogen atom, ethenyl, 2-carboxyethenyl, chlorine, methoxy, or a group represented by —CH$_2$Y, wherein Y represents a hydrogen atom or a nucleophilic compound residue, Z represents a hydrogen atom, a metal atom, or an alkyl group having 1 to 5 carbon atoms, an aryl group having 6 to 10 carbon atoms, a cycloalkyl group having 6 to 10 carbon atoms, or an aralkyl group having 7 to 20 carbon atoms; and A represents =CH— or =N—, E represents —S— or —O—; Q represents =O or a functional group represented by =N~R$^4$, wherein R$^4$ represents a hydroxy group or an alkoxy group and ~ in =N~R$^4$ represents syn- or anti-form, wherein said dehydration condensing agent is a carbodiimide represented by formula:

$$R^1-N=C=N-R^2$$

wherein R$^1$ and R$^2$, which may be the same or different, each represents an alkyl group having 1 to 5 carbon atoms, an aryl group having 6 to 10 carbon atoms, a cycloalkyl group having 6 to 10 carbon atoms, or an aralkyl group having 7 to 20 carbon atoms, and wherein said acid or acid complex is a sulfonic acid represented by R$^3$SO$_3$H, a hydrohalogen acid represented by HX, a Lewis acid, or a Lewis acid complex; wherein R$^3$ represents a hydroxy group, an alkyl group having 1 to 5 carbon atoms, an aryl group having 6 to 10 carbon atoms, a cycloalkyl group having 6 to 10 carbon atoms, or an aralkyl group having 7 to 20 carbon atoms; and X represents a halogen atom.

2. The process of claim 1, wherein said reacting is carried out in a solvent selected from the group consisting of a halogen-containing organic solvent, an alcoholic organic solvent, a ketone organic solvent, and ether organic solvent, an ester organic solvent, and mixtures thereof.

* * * * *